(12) United States Patent
Flint et al.

(10) Patent No.: US 9,724,371 B2
(45) Date of Patent: *Aug. 8, 2017

(54) FEEDLOT ADMINISTERED BACTERIAL COMPOSITION

(71) Applicant: MicroBios, Inc., Houston, TX (US)

(72) Inventors: Joseph F. Flint, Ithaca, NY (US); Matthew Ryan Garner, Amarillo, TX (US)

(73) Assignee: MICROBIOS, INC., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/575,949

(22) Filed: Dec. 18, 2014

(65) Prior Publication Data

US 2015/0104419 A1    Apr. 16, 2015

(51) Int. Cl.
| | | |
|---|---|---|
| *A01N 63/00* | (2006.01) | |
| *A61K 35/747* | (2015.01) | |
| *A61K 35/742* | (2015.01) | |
| *A61K 35/744* | (2015.01) | |

(52) U.S. Cl.
CPC .......... *A61K 35/747* (2013.01); *A61K 35/742* (2013.01); *A61K 35/744* (2013.01); *A23Y 2220/07* (2013.01); *A23Y 2280/15* (2013.01)

(58) Field of Classification Search
None
See application file for complete search history.

(56) References Cited

U.S. PATENT DOCUMENTS

2007/0286844 A1   12/2007   McGrath et al.

OTHER PUBLICATIONS

Malago et al. ; Microbial Products from Probiotic Bacteria inhibit *Salmonella enteritidis* 857-Induced IL-8 Synthesis in Caco-2 Cells; 2010 vol. 55, No. 4, p. 401-408.
Non-Final Office Action mailed Feb. 24, 2015; in U.S. Appl. No. 14/587,705.

*Primary Examiner* — Kade Ariani
(74) *Attorney, Agent, or Firm* — Polsinelli PC

(57) ABSTRACT

A feedlot administered animal feed additive that promotes animal health and growth, reduces mortality and can act as an antibiotic substitute. The additive inhibits pathogen growth resulting in lower pathogen load within the animal and reduced pathogen sheading to the environment. The additive includes bacteria that inhibit *E. coli* O157:H7 growth by as much as 93% and *Salmonella* growth by as much as 97%, together with commensurate inhibition rates against the Big-Six *Escherichia coli* strains. The additive includes various combinations of the following pathogen-inhibiting bacteria: *Lactobacillus animalis; Enterococcus faecium*; and *Pediococcus acidilactici*.

26 Claims, 3 Drawing Sheets

Percent Pathogen Growth Inhibition by Combination Composition

| Inhibition Composition | | Percent Inhibition By Pathogen Strain | | |
| --- | --- | --- | --- | --- |
| Genus | Strain | E. coli O157:H7 | Salmonella typhimurium | Salmonella enteriditis |
| Lactobacillus animalis<br>Lactobacillus animalis<br>Pediococcus acidilactici<br>Enterococcus faecium | MB101<br>MB102<br>MB902<br>MB505 | 93.1% | 97.4% | 96.0% |
| Lactobacillus animalis<br>Pediococcus acidilactici | MB101<br>MB902 | 92.7% | 96.3% | 95.4% |
| Lactobacillus animalis<br>Enterococcus faecium | MB101<br>MB505 | 92.1% | 95.8% | 95.4% |
| Lactobacillus animalis<br>Lactobacillus animalis | MB101<br>MB102 | 91.9% | 91.1% | 95.3% |
| Lactobacillus animalis<br>Pediococcus acidilactici<br>Enterococcus faecium | MB102<br>MB902<br>MB505 | 91.6% | 90.7% | 94.8% |
| Lactobacillus animalis<br>Lactobacillus animalis<br>Enterococccus faecium | MB101<br>MB102<br>MB505 | 90.9% | 90.0% | 94.0% |
| Lactobacillus animalis<br>Lactobacillus animalis<br>Pediococcus acidilactici | MB101<br>MB102<br>MB902 | 90.8% | 89.7% | 94.0% |
| Pediococcus acidilactici<br>Enterococcus faecium | MB902<br>MB505 | 86.5% | 87.3% | 91.7% |
| Lactobacillus animalis<br>Enterococcus faecium | MB102<br>MB505 | 86.3% | 87.1% | 90.8% |
| Lactobacillus animalis<br>Pediococcus acidilactici<br>Enterococcus faecium | MB101<br>MB902<br>MB505 | 85.7% | 87.0% | 90.5% |
| Lactobacillus animalis<br>Pediococcus acidilactici | MB102<br>MB902 | 84.8% | 82.7% | 87.9% |

FIG. 2

Percent Pathogen Growth Inhibition by Individual Bacteria

| Inhibition Composition | | Percent Inhibition By Pathogen Strain | | | | | | | |
|---|---|---|---|---|---|---|---|---|---|
| Genus | Strain | E. coli O157:H7 | E. coli O121:H19 | E. coli O45:H2 | E. coli O103:H11 | E. coli O145 | E. coli O26:H11 | E. coli O111 | Salmonella typhimurium | Salmonella enteritidis |
| Lactobacillus animalis | MB101 | 93.9% | 96.3% | 94.4% | 92.8% | 93.0% | 91.9% | 85.0% | 97.9% | 97.2% |
| Lactobacillus animalis | MB102 | 90.1% | 91.2% | 90.8% | 94.7% | 87.4% | 89.3% | 85.9% | 87.8% | 93.9% |
| Enterococcus faecium | MB505 | 88.2% | 86.6% | 70.1% | 88.2% | 87.5% | 86.9% | 89.8% | 87.8% | 92.3% |
| Pediococcus acidilactici | MB902 | 85.2% | 88.2% | 88.6% | 91.5% | 86.0% | 87.3% | 86.4% | 68.3% | 87.3% |

FIG. 3

FEEDLOT ADMINISTERED BACTERIAL COMPOSITION

FIELD

The present disclosure relates generally to compositions and methods for manufacture and use of feedlot administered pathogen inhibiting bacterial compositions.

BACKGROUND

Certain bacteria have been recognized for their capability to inhibit the growth of certain pathogenic bacteria, and have therefore been utilized as additives in products for which pathogenic inhibition is advantageous. At least one example is animal feed to which bacteria are sometimes added and that have been found to improve animal efficiency and health. Such bacterial feed additives are frequently referred to as probiotics, as well as Direct Fed Microbials, or DFMs.

BRIEF DESCRIPTION OF THE DRAWINGS

Implementations of the present technology will now be described, by way of example only, with reference to the attached figures, wherein:

FIGS. 2 and 3 are tables detailing discovered pathogen inhibition efficiencies of the bacteria and bacterial compositions disclosed herein.

DETAILED DESCRIPTION

Figure 1:
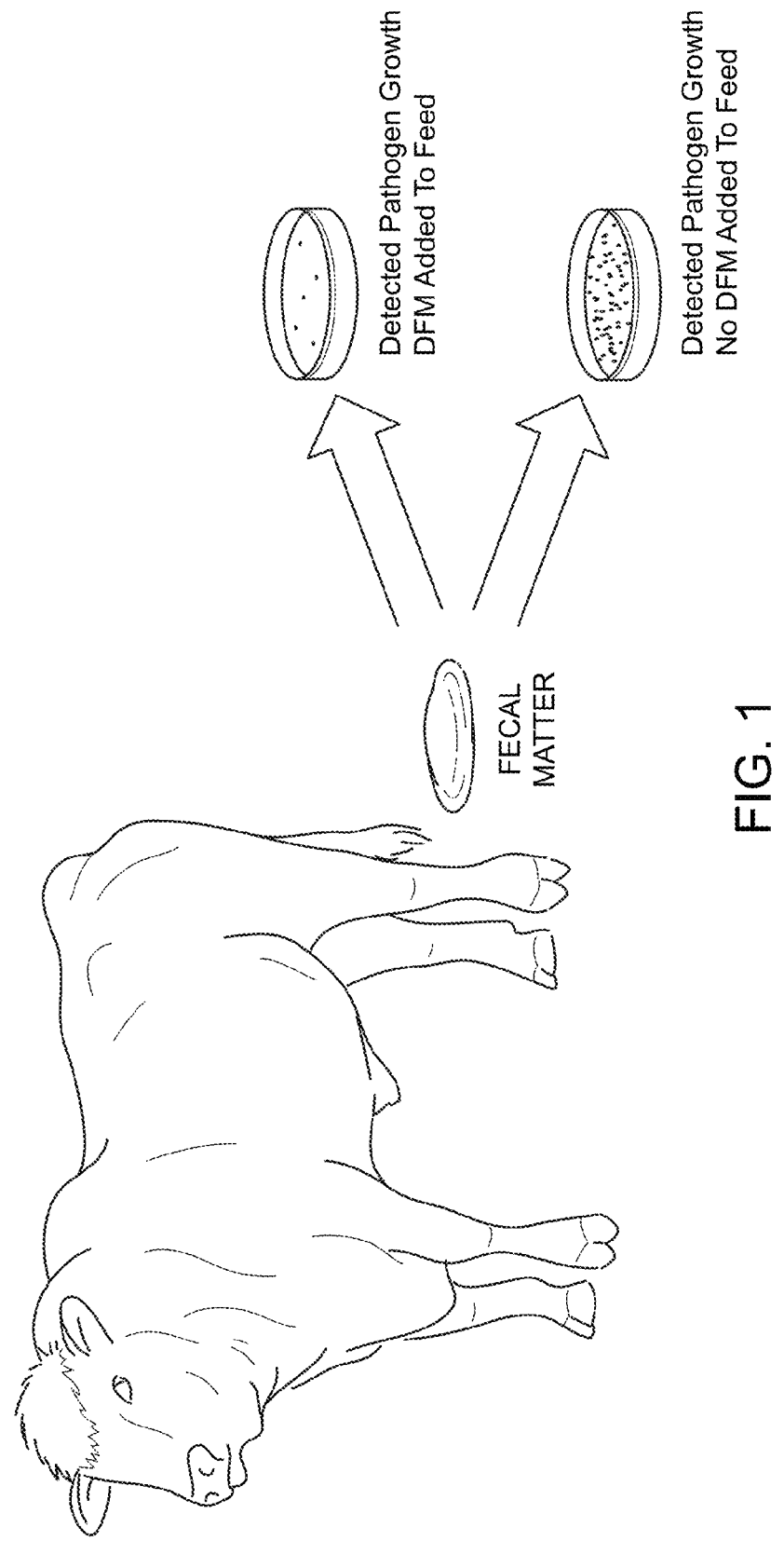
FIG. 1 is a diagram representing pathogen inhibition in a feedlot housed animal by the administration of the bacterial compositions disclosed herein.

One of the larger economic burdens facing cattle owners is the high cost of rearing and/or replacing animals to maintain or increase herd size. A major factor contributing to the high cost of cattle replacement is the prevalence of diarrheal disease, known as scours, in livestock. Scours causes greater than 60% of all deaths associated with pre-weaned calves, and accounts for 6.2% of total calf losses. The prevalence of scours can vary dramatically (4.3% to 52.4%) depending on herd, diet, season, or "outbreak" occurrences. Estimates of scouring rates within a herd are difficult to obtain, though they are believed to between 15% and 35%. Nonetheless, it is agreed that diarrheal events comprise the largest health challenge to pre-weaned calves.

Moreover, diarrhea (scours) remains the predominant cause of mortality among calves. There are multiple causes of scours including malabsorption and improper nutrition; however, infections by bacteria, viruses, and protozoa are the primary etiological agents. It is important to consider that scours in calves may be due to a number of concurrent gastrointestinal insults by numerous pathogens. Susceptibility to acute undifferentiated diarrhea can be largely determined by the quantity, quality, and administration time of colostrum.

The costs associated with scours are difficult to estimate; however, mortality alone represents a large expense, since, at birth, a heifer has an estimated value of $400-$600. Scours does not always result in death, but costs associated with treatment (e.g. electrolytes, antibiotics, veterinary services and associated labor) can be significant. In addition, animal sickness and death can negatively impact the morale of farm laborers and must be taken into consideration, though the financial costs of this cannot be readily quantified.

Serum immunoglobulin obtained from colostrum can offer some limited protection to calves from bacterial and viral infections. However, this protective effect begins to diminish <96 hours after birth, which could explain the high onset of viral scours 5-7 days following birth. Prophylactic antibiotics and vaccines administered to calves are frequent measures used to prevent scours in calves. While antibiotic administration can be effective against bacterial infections, antibiotics are ineffective against viruses and protozoa and, in fact, they can promote the development of viral or protozoal scours by diminishing the normal protective flora. Moreover, the use of antibiotics is disfavored in many settings and can otherwise compromise the health and/or value of the animal. Vaccinations can also confer protection against scours; however, the full protective immune response does not occur until after a few weeks of administration. Despite some advances in prevention and treatment, the incidence of scours can vary wildly between cattle herds.

A major factor contributing to the onset of scours in calves is the practice of removing calves from their mother cows immediately after birth, and transporting them to facilities away from adult animals. The gastrointestinal tracts of mammals, including calves, are sterile at birth, but rapidly become colonized by microflora located near the mother's vagina and anus. Other bacteria begin to establish themselves when the neonate comes into contact with new objects (feed, dirt, gates, fences, handlers, etc.). Prior to the current practice of removing a calf from its mother, protective microflora would become established in the calf due to contact with the mother via licking, nursing, and grooming. Thus, one possible avenue to reduce the incidence and severity of scours includes manipulating the bacterial flora of a calves' digestive tract.

It has long been known that a number of beneficial bacteria colonize the intestinal tracts of mammals and can promote the well-being of the host. It has also been recognized for many years that the consumption of exogenous bacteria, often referred to as probiotics, can elicit beneficial effects upon a host. In humans, these probiotic bacteria have been shown to reduce the severity and duration of rotaviral-induced diarrhea, alleviate lactose intolerance, and enhance gastrointestinal immune function. Traditionally, food sources such as yogurt have been considered probiotic-carriers providing these health-promoting benefits. It is believed that the consumption of foods rich in probiotic bacteria, including lactic acid bacteria and bifidobacteria, leads to colonization of the human gastrointestinal tract of humans.

The consumption of probiotics by animals used in food production can improve their health and feed utilization efficiencies, as well as decrease certain pathogen loads within the animal and pathogen sheading outside, from the animal. Probiotics work by competitive exclusion in which live bacterial cultures act antagonistically on specific organisms to cause a decrease in the numbers of that organism. Mechanisms of competitive exclusion include production of antibacterial agents (bacteriocins) and metabolites (organic acids and hydrogen peroxide), competition for nutrients, and competition for adhesion sites on the gut epithelial surface. Lactic acid producing bacteria are generally considered as food grade organisms and there are many potential applications of protective cultures in various foods. A number of different factors have been identified that contribute to the antibacterial activity of lactic acid producing bacteria. These bacteria produce different antibacterials, such as lactic acid, acetic acid, hydrogen peroxide, carbon dioxide and bacteriocins, which can inhibit pathogenic microorganisms.

A majority of bacteriocins produced by bacteria are lantibiotics or small hydrophobic heat stable peptides. Nisin, a lantibiotic is effective at inhibition of Gram-positive bacteria such as *Bacillus* and *Clostridium*. However, Nisin has demonstrated no effectiveness against Gram-negative bacteria. Among the small hydrophobic heat stable peptides, pediocins are frequently encountered and possess the ability to inhibit *Listeria monocytogenes*.

*Lactobacillus* genus includes the most prevalently administered probiotic bacteria. *Lactobacillus* is a genus of more than 25 species of gram-positive, catalase-negative, non-sporulating, rod-shaped organisms. *Lactobacillus* species ferment carbohydrates to form lactic acid. *Lactobacillus* species are generally anaerobic, non-motile, and do not reduce nitrate. *Lactobacillus* species are often used in the manufacture of food products including dairy products and other fermented foods. *Lactobacillus* species inhabit various locations including the gastrointestinal tracts of animals and intact and rotting plant material. *Lactobacillus* strains appear to be present in the gastrointestinal tract of approximately 70% of humans that consume a Western-style diet. The number of *Lactobacillus* cells in neonates is approximately 105 colony forming units (CFU) per gram CFU/g of feces. The amount in infants of one month and older is higher, ranging from 106 to 108 CFU/g of feces.

Lactic acid and products containing lactic acid enhance gains in the starting period of feedlot cattle (first 28 days) and reduce liver abscesses when administered during the transition from a primarily roughage diet of grass to a feedlot diet including more grains. Certain strains of *Lactobacillus acidophilus* have been isolated which restore and stabilize the internal bacterial balance of animals. Some strains demonstrate a greater propensity to adhere to the epithelial cells of some animals which would increase their ability to survive, initiate and maintain a population within an animal intestine. Thus, the primary mode of action as previously understood relative to *Lactobacillus acidophilus* occurs post-ruminally.

The most common method used today to control pathogenic populations in livestock is through the use of antibacterial compounds. While these are effective for short-term treatments, prolonged application of antibacterial compounds leads to the evolution of antibiotic resistance in the pathogenic organisms. The widespread occurrence of antibiotic resistant microorganisms is well known; two examples are methicillin resistant *Staphylococcus aureus* (MRSA) and vancomycin resistant enterococci (VRE). Bacteria are remarkably adaptable to deleterious environments with their abilities to rapidly reproduce and modify their genetic content. Thus, it is inevitable that after prolonged application of any method that disrupts or kills bacteria, a population that is recalcitrant to its effects will eventually arise. It is not uncommon now in the veterinary environment that doctors often resort to using multiple antibiotics concurrently or in succession to eradicate pathogenic organisms.

As with antibiotics, bacteria can also become resistant to other biological treatments. For example, bacteriophages are able to reduce pathogen populations, but inevitably, a fraction of the targeted bacterial population is not affected. This small sub-population then rapidly reproduces and attains sizable population numbers.

Similar circumstances have been seen with the application of probiotic bacteria that are meant to inhibit or reduce the numbers of pathogenic bacteria within a gastrointestinal system. Some researchers have commented that significantly better animal performance and pathogen reductions were seen in treated animals early in their experiments, but the beneficial effects were no longer statistically different after prolonged application of the probiotic product. It is possible that the target populations were initially affected, but prolonged usage of the probiotic product led to the selection of bacterial populations that were not influenced by the application of the product. According to this disclosure, the adaptation of pathogens to probiotic treatment can be avoided with the inclusion of multiple strains of bacteria.

There are numerous advantages provided by the inclusion of multiple strains of bacteria in a bacterial composition such as that which is disclosed herein. These advantages, whether working independently or concurrently, support the superiority of the presently disclosed bacterial composition and the enhanced benefits for an animal to which it is administered.

Different bacteria strains utilize certain nutrients more efficiently than others. The ability to use available nutrients in a gut environment is necessary for the bacteria to produce antibacterial compounds or to beneficially affect the host GI system. However, the nutrient availability is constantly changing because of animal behavior, different foods consumed, antibiotic use, energy requirements, or health of the animal. These fluctuations allow different bacteria to proliferate while other bacterial populations diminish.

The use of different bacterial strains also produces different bacterial metabolites. Different metabolites have different effects upon pathogenic populations. Lactic acid is a powerful antibacterial agent against some pathogens, while propionic acid is more effective against other populations. It should also be considered that just as metabolites produced from cells in bacterial products affect GI populations, endogenous microorganisms produce chemicals that can be inhibitory to some bacteria strains. The present inclusion of different strains in a direct fed feed supplement increases the likelihood that the product will have a positive effect.

Additionally, the production of bacteriocins influences bacterial populations. There is a large diversity of bacteriocins that target specific bacteria populations. Thus, a bacterial product that contains multiple strains will produce multiple bacteriocins and target different groups of pathogenic populations. Conversely, the intestinal tract contains a large diversity of bacteriocin producing bacteria. While some of the produced bacteriocins can affect one of the included strains, it is unlikely to affect all of the included microorganisms.

Another benefit of the presently disclosed multi-strain bacterial composition when utilized as a direct fed feed additive is its ability to target more than one pathogen population for inhibition. Bacterial pathogens are very diverse and require different methods to reduce or eliminate their populations. Thus, a product containing different pathogen inhibiting bacteria that are able to effect different pathogenic populations will result in an overall healthier animal and herd.

Different microorganisms positively influence the gastrointestinal system through different mechanisms. Therefore, including bacteria that work through different modes will result in a superior product. One strain may reduce pathogen populations, while another has an immunostimulative effect, while another produces micronutrients essential for the host. Interestingly, multiple strains can also provide synergistic effects upon the host or pathogen inhibition abilities. One strain alone may not be able to reduce certain populations, but the combination of two or more different strains working through different mechanisms can reduce pathogen populations.

Additionally, the use of multiple beneficial microorganisms can help overcome bacteriophages that infect and kill bacteria. Bacteriophages are very common in gastrointestinal systems and have profound effects upon the bacterial community. Bacteriophages require specific sites on a cell to bind and infect. Thus, by including multiple microorganisms in a product, the greater the likelihood that at least some populations from the product will evade bacteriophage attack and elicit beneficial effects upon the bacterial community and host.

Certain examples in the present disclosure concern a method of inhibiting or reducing a population of pathogenic bacteria in, on and/or outside the animal. In one aspect, the disclosed compositions reduce a population of pathogenic bacteria in the gastrointestinal tract of the animal.

Other examples concern the inhibition or reduction of a population of pathogenic bacteria by providing to the animal a composition containing the multiple probiotic bacteria described herein.

In the examples of the present disclosure wherein an administration of pathogen inhibiting bacteria is contemplated, the number of bacteria (concentration) per administration can be any amount capable of providing some inhibition or reduction of a population of pathogenic bacteria. In specific embodiments, the number of bacteria per administration is between $1\times10^3$ and $1\times10^9$ bacteria. Preferably, the number of bacteria in an administration is approximately $1\times10^6$ bacteria.

The administrations can be timed such that a series of administrations of the composition or its separate components is separated by 1, 2, 3, 4, 5, 6, 7, 8, 9, 10, 11, 12, 13, 14, 15, 16, 17, 17, 19, 20, 21, 22 or 23 hours or 1, 2, 3, 4, 5, or 6 days or 1, 2 or 3 weeks or 1 month or some duration in between. In some specific embodiments, the administrations are daily.

Among others, administration of the bacterial composition to the animal can be oral, nasal, topical, rectal, and via injection. In certain embodiments, the administrations are oral administrations. In embodiments wherein the administrations are oral administrations, the composition comprising probiotic bacteria can be mixed with animal feed or mixed with animal drinking water. In such embodiments, the composition or compositions can be formulated as a liquid formulation for administration, or as a freeze dried formulation, or as a gel formulation or as a spore formulation.

Additional steps in inhibiting or reducing the population of pathogenic bacteria in an animal include assessing the presence of pathogenic bacteria in the gastrointestinal tract of the animal between administrations. In more specific embodiments, the animal is assessed for the presence of pathogenic bacteria, for strains of pathogenic bacteria, species of pathogenic bacteria and number (concentration) of pathogenic bacteria present. In specific embodiments, this assessment is done by examining the feces of the animal.

In the context of the present disclosure, the terms "substantially" and "about" are defined to be essentially conforming to the particular quantity, concentration, dimension, shape or other thing that "substantially" or "about" modifies, such that the so described characteristic need not be exact, but within reasonable tolerances. The terms "comprising," "including" and "having" (and variants thereof) are used interchangeably in this disclosure. The terms "comprising," "including" and "having" mean to include, but not necessarily be limited to the things so described.

It should be understood that this disclosure is not limited to particular compositions or biological systems, which can, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which the disclosure belongs. Although any methods and materials similar or equivalent to those described herein can be used in the practice or testing of the present disclosure, the preferred methods and materials are now described.

In this specification and the claims that follow, reference will be made to a number of terms which can be considered to have the following meanings: "inhibit" and/or "reduce" or other forms of the words and their synonyms, such as "reducing" or "reduction," refer to slowing the growth of the so-referenced pathogen and/or lowering its incidence. It is understood that this is typically in relation to some standard or expected value, in other words it is relative, but that it is not always necessary for the standard or relative value to be referred to. For example, "reduces the population of bacteria" in certain instances refer to lowering the amount of bacteria relative to a standard or a control. "Inhibit" and "inhibition" refer to slowing or deterring pathogen growth, including pathogenic bacterial growth that would have otherwise occurred except for the provision of the characterized deterrent.

By "treat" or other forms of the word, such as "treated" or "treatment," means to administer a composition or to perform a method in order to reduce, prevent, inhibit, break-down, or eliminate a particular characteristic or event.

The term "viable cell" means a microorganism, and in particular, bacteria that are alive and capable of regeneration and/or propagation, while in a vegetative, frozen, preserved, or reconstituted state.

The term "viable cell yield" or "viable cell concentration" refers to the number of viable cells in a liquid culture, concentrated, or preserved state per a unit of measure, such as liter, milliliter, kilogram, gram or milligram.

The term "cell preservation" refers to a process that takes a vegetative cell and preserves it in a metabolically inert state that retains viability over time. As used herein, the term "product" refers to a bacterial composition that can be blended with other components and contains specified concentration of viable cells that can be sold and used.

As used herein, the terms "microorganism" or "microbe" refers to an organism of microscopic size. The definition of microorganism herein includes bacteria, Archaea, single-celled Eukaryotes (protozoa, fungi, and ciliates), and viral agents (viruses). The term "microbial" is used herein to describe processes or compositions of microorganisms, thus a "microbial-based product" is a composition that includes microorganisms, cellular components of the microorganisms, and/or metabolites produced by the microorganisms. Microorganisms can exist in various states and occur in vegetative, dormant, or spore states. Microorganisms can also occur as either motile or non-motile, and may be found as planktonic cells (unattached), substrate affixed cells, cells within colonies, or cells within a biofilm.

The term "bacteria" refers to one-celled organisms that are Prokaryotes in that their genetic material, or DNA, is not enclosed in a nucleus.

The term "prebiotic" refers to food ingredients that are not readily digestible by endogenous host enzymes and confer beneficial effects on an organism that consumes them by selectively stimulating the growth and/or activity of a limited range of beneficial microorganisms that are associated with the intestinal tract.

The term "probiotic" refers to one or more live microorganisms that confer beneficial effects on a host organism. Benefits derived from the establishment of probiotic microorganisms within the digestive tract include reduction of pathogen load, improved bacterial fermentation patterns, improved nutrient absorption, improved immune function, aided digestion and relief of symptoms of irritable bowel disease and colitis.

The term "synbiotic" refers to a composition that contains both probiotics and prebiotics. Synbiotic compositions are those in which the prebiotic compound selectively favors the probiotic microorganism.

The term "gastrointestinal tract" refers to the complete system of organs and regions that are involved with ingestion, digestion, and excretion of food and liquids. This system generally consists of, but not limited to, the mouth, esophagus, stomach and or rumen, intestines (both small and large), cecum (plural ceca), fermentation sacs, and the anus.

The term "pathogen" refers to any microorganism that produces a harmful effect and/or disease state in a human or animal host.

The term "fermentation" refers to a metabolic process performed by an organism that converts one substrate to another in which the cell is able to obtain cellular energy, such as when an organism utilizes glucose and converts it to lactic acid or propionic acid. Many of the end-substrates formed in fermentation processes are volatile fatty acids.

The term "volatile fatty acids" (VFAs) refers to short-chain fatty acids containing six or fewer carbon atoms and at least one carboxyl group. Some examples of VFAs include, but are not limited to: lactic acid, acetic acid, propionic acid, butyric acid, isobutyric acid, valeric acid, and isovaleric acid, which are products of bacterial fermentation within the digestive tracts of animals. Volatile fatty acids can be absorbed through the intestines of animals and used as an energy or carbon source. Bacteria produce VFAs based on available substrates and also rely upon VFAs for energy and carbon sources.

The term "lactic acid" refers to a byproduct of glucose fermentation resulting in a three-carbon acid with the chemical formula $C_3H_6O_3$. This includes, but is not limited to, lactic acid derived from specific strains of bacteria or lactic acid derived from other types of organisms. Lactic acid can be microbialstatic, microbialcidal, bacteriostatic, bacteriocidal or bacteriolytic; these concepts are known to skilled persons. "Lactic acid producing" refers to any organism that generates lactic acid.

The term "bacteriocin(s)" refers to (poly) peptides and proteins that inhibit one or more bacterial species. This includes, but is not limited to, (poly) peptides or proteins that were derived from specific strains of bacteria or (poly) peptides that are derived from other types of organisms.

The bacteriocin can be microbialstatic, microbialcidal, bacteriostatic, bacteriocidal, or bacteriolytic; these concepts are known to skilled persons. For the treatment of produce and other food products the bacteriocin is preferably microbialcidal or bacteriocidal. "Bacteriocin producing" in certain instances refer to any organism that generates bacteriocins.

As used herein, "hydrogen peroxide" refers to a byproduct of oxygen metabolism that has the chemical formula $H_2O_2$. This includes, but is not limited to, hydrogen peroxide derived from specific strains of bacteria or hydrogen peroxide derived from other types of organisms. Hydrogen peroxide can be microbialstatic, microbialcidal, bacteriostatic, bacteriocidal or bacteriolytic; these concepts are known to skilled persons. "Hydrogen peroxide-producing" refers to any organism that generates hydrogen peroxide.

As used herein, the term "synergistic" refers to a property wherein the combined result of two effects is greater than would be expected if the two effects were added together. The term "synergistically" is used to describe a synergistic effect.

As used herein, the phrase "foregut fermentor" refers to an animal having an anatomical compartment in the alimentary canal that is positioned anterior to the stomach that is used for bacterial fermentation and digestion of ingested materials. Ruminal fermentors are considered foregut-fermenting organisms.

As used herein, the phrase "ruminal fermentor" or "rumen fermenting" refers to an animal having a large, multi-compartmented section of the digestive tract, called a rumen, which is positioned between the esophagus and the anus. Rumen are very complex ecosystems that support bacterial fermentation of cellulose, plant matter, and other ingested materials. Ruminal-fermentors may also be termed "cranial fermentors" or "ruminants". Some examples of rumen-fermenting organisms include cattle, sheep, goats, camels, llama, bison, buffalo, deer, wildebeest and antelope.

As used herein, the phrase "hindgut fermentor" refers to an animal having a complex large intestine that may or may not include specialized fermentation chambers that can include a cecum or blind sac, that is positioned posterior to the stomach in the alimentary canal. Cecal fermentors and intestinal fermentors are both considered hindgut-fermenting organisms.

As used herein, the phrase "cecal fermentor" refers to an animal having a complex large intestine that includes a cecum or a blind sac along the digestive tract. The cecum of a cecal fermentor forms a distinct chamber, which is the primary site of bacterial fermentation of cellulose, plant matter, or other ingesta. A cecal-fermentor may also be referred to as "caudal fermentor". Cecal-fermentors include horses, elephants, rabbits, mice, rats, guinea pigs and the like.

As used herein, the term "intestinal fermentor" refers to an animal that does not primarily rely upon bacterial fermentation of ingesta in a rumen or large cecum. In the digestive tracts of intestinal fermentors, bacterial fermentation occurs primarily within the large intestine or colon. Intestinal fermentors include chickens, pigs, humans and the like.

As used herein, the term "monogastric" refers to an animal having a single, simple (single chambered) stomach. Typically, cecal fermentors and intestinal-fermentors are monogastric animals. Some examples of monogastric animals include horses, chickens, pigs, humans and the like.

As used herein, the term "polygastric" refers to an animal having a multiple, complex (multi-chambered) stomachs. Ruminal fermentors are polygastric animals.

As used herein, the phrase "pre-gastric fermentation" refers to bacterial fermentation that occurs before the food reaches a 'true' stomach, which is generally the site of gastric acid and digestive enzyme secretion. Ruminants are pre-gastric fermentors.

As used herein, the phrase "post-gastric fermentation" refers to bacterial fermentation that occurs after food passes through a stomach, which is generally the site of gastric acid and digestive enzyme secretion. Hindgut fermentors, including cecal fermentors and intestinal fermentors, utilize post-gastric fermentation.

As used herein, the term "herbivore" refers to an animal that exclusively consumes plant material.

As used herein, the term "omnivore" refers to an animal that consumes both plant and animal material.

As used herein, the term "carnivore" refers to an animal that exclusively consumes animal material.

As used herein, "digesta" refers to food or any other material that enters the alimentary canal and undergoes, completely or partially, through the process of being digested or broken down into smaller components.

The present specification discloses a novel composition variously comprised of multiple bacteria strains. The composition can be added to products to inhibit pathogen growth and/or reduce pathogen presence in downstream production processes, product storage and/or product utilization. Among other uses, the composition can be utilized in washes, dips and the like for reducing pathogen load and inhibiting pathogen growth; for instance, in and on food products. Surfaces such as countertops, refrigerators and food preparation surfaces can also be treated, with special benefits being provided to porous surfaces into which the composition can be absorbed.

The presently disclosed compositions are particularly advantageous when ingested as a probiotic supplement or utilized as a direct fed bacterial feed additive that provides beneficial effects to all types of animals, including amphibians, birds, fish, invertebrates, reptiles and mammals, including fermentors, cecal fermentors and intestinal fermentors. In one embodiment, the probiotic formulation supplemented with prebiotic compounds is fed to ruminal fermentors to reduce scours events and improve animal health. Ruminal fermentors that can benefit from the present disclosure include but are not limited to: cattle, sheep, goats, camels, llama, bison, buffalo, deer, wildebeest, antelope, and any other pre-gastric fermentor.

In another embodiment, the probiotic formulation supplemented with prebiotic compounds is fed to cecal fermentors to reduce scours events and improve animal health. Cecal fermentors that can benefit from this disclosure include but are not limited to: horses, ponies, elephants, rabbits, hamsters, rats, hyraxes, guinea pigs, and any other post-gastric fermentor that using the cecum as the primary location of fermentative digestion. In another embodiment, the probiotic formulation supplemented with prebiotic compounds is fed to intestinal fermentors to reduce scours events and improve animal health. Intestinal fermentors that can benefit from said disclosure include but are not limited to: humans, pigs, chickens, and other post-gastric fermentor using the large intestine as the primary location of fermentative digestion. In each case, the composition is packaged in a format that ensures survival of both the probiotic and prebiotic components into the gastrointestinal system of the animal.

In one aspect, the present disclosure provides a novel composition that reduces animal mortality and morbidity and reduces pathogen load in the animal, as well as pathogen sheading in its feces. Administration of the bacteria-based compositions to the animal also can improve animal health and/or productivity by way of increased feed efficiency. It also provides a composition that will be used once, periodically or on a continual basis to reduce the incidence and severity of scours and/or improve animal health. The composition is durable and easy to apply to animal feed or other easily ingestible materials.

The novel compositions disclosed comprise specially selected bacteria, at least some of which can produce lactic acid which inhibits the growth of pathogenic organisms during digestive fermentation. The composition can comprise a mixture of lactic acid producing bacteria. In some embodiments, the composition is mixed with colostrum or milk replacers. In other embodiments the mixture is applied to milk or water administered to calves. Animals can be treated with a combination of viable microorganisms with prebiotic compounds to improve animal efficiency and/or health. Additive, or more preferably super-additive or more preferably synergistic effects can be achieved with the administration of two or more bacteria species and/or strains. Animals can be treated once, multiple times, or therapeutically on a daily basis.

In one aspect, various compositional examples of this disclosure include bacterial combinations that are pathogen inhibitive in that the combination inhibits pathogen growth when added thereto. The specially selected bacteria can be of different species (for example, *L. animalis* versus *Enterococcus faecium*), or they may be of the same species (for example, *L. animalis* and *L. animalis*) but different strains (for example, MB101 and MB102) within the same species (*L. animalis*). That is to say, the composition may contain multiple species and/or multiple strains. For example, two, three, four, five, six, and so on different bacterial strains can be included. The use of multiple types of the specially selected bacterial strains lead to a superiorly reliable product for maintaining or improving animal health or inhibiting, decreasing or eliminating the presence of pathogenic bacteria. As an example, each of the bacteria in the composition can have superior survival characteristics under various conditions likely to be encountered during storage, transport and/or administration. In that way it is better assured that viable bacteria will reach the target (animal, object and the like), regardless of whether one or more abusive conditions (such as overheating) have been encountered after manufacture.

More specifically, among others, four different pathogen inhibiting bacteria strains have been discovered and are variously included in the instantly disclosed bacterial compositions. Each strain was deposited on Nov. 7, 2014 with the American Type Culture Collection (ATCC) located at ATCC Patent Depository, 10801 University Blvd., Manassas, Va. 20110 and the corresponding certificates issued on Nov. 25, 2014 carrying the title of Budapest Restricted Certificate of Deposit Budapest Treaty on the International Recognition of the Deposit of Microorganisms for the Purpose of Patent Procedure International Form Receipt in the Case of an Original Deposit Issued Pursuant to Rule 7.3 and Viability Statement Issued Pursuant to Rule 10.2. The deposits, their taxonomic descriptions, dates of deposit and accession numbers have been certified as follows:

| Strain Name | Genus | Date Deposited | ATCC Accession Number |
|---|---|---|---|
| MB505 | *Enterococcus faecium* | Nov, 07, 2014 | PTA-121709 |
| MB101 | *Lactobacillus animalis* | Nov, 07, 2014 | PTA-121710 |
| MB102 | *Lactobacillus animalis* | Nov, 07, 2014 | PTA-121711 |
| MB902 | *Pediococcus acidilactici* | Nov, 07, 2014 | PTA-121712 |

In FIG. 2 of the present disclosure, specific compositional combinations of the discovered strains are disclosed together with their derived pathogen inhibition efficacies specified in terms of percent pathogen growth inhibition determined using the processes described below. The derived pathogen inhibition efficacies of the individual strains are shown in FIG. 3.

Experiments demonstrating the ability of the strains to inhibit the growth of pathogenic organisms were performed using the following method. A "control" tube was prepared containing an amount of modified MRS medium to which an amount {concentration at 1×10$^6$ CFU/ml} of a single strain pathogenic bacteria {*E. coli* or *Salmonella*, for example} was added. A "challenged" tube was prepared that contained the same amount of the modified MRS medium to which the same amount of the single strain pathogenic bacteria was added as in the control tube, together with an equal total amount {concentration at 1×10$^6$ CFU/ml} of challenging bacterium strain(s) as the pathogenic bacteria. The tubes were placed into a water bath at 37° C. and incubated for six hours. After incubation, each tube was serially diluted and 100 microliters of its content spread onto Luria-Bertani plates to enumerate the number of viable pathogen cells. The percent pathogen growth inhibition was then calculated as: the difference between the amount of viable pathogen cells in the challenged tube versus the control tube, divided by the amount of viable pathogen cells in the control tube, and then multiplied by 100.

Similar illustrative procedures are disclosed and described in US Patent Publication 2011-0189132, the entirety of which is hereby incorporated herein by reference.

New compositions that deliver pathogen growth inhibition are variously disclosed in FIG. 2, including those that comprise at least two of any of the following four bacteria: (1) *Lactobacillus animalis* strain MB101 having ATCC Accession Number PTA-121710; (2) *Lactobacillus animalis* strain MB102 having ATCC Accession Number PTA-121711; (3) *Enterococcus faecium* strain MB505 having ATCC Accession Number PTA-121709; and (4) *Pediococcus acidilactici* strain MB902 having ATCC Accession Number PTA-121712.

Exemplarily, a composition is described that includes (1) *Lactobacillus animalis* strain MB101 having ATCC Accession Number PTA-121710 and (2) *Lactobacillus animalis* strain MB102 having ATCC Accession Number PTA-121711. The composition demonstrated the following pathogen inhibition percentages: 91.9% inhibition of *E. coli* O157:H7; 91.1% inhibition of *Salmonella typhimurium* and 95.3% inhibition of *Salmonella enteriditis*.

Another composition is described that includes (1) *Lactobacillus animalis* strain MB101 having ATCC Accession Number PTA-121710; (2) *Lactobacillus animalis* strain MB102 having ATCC Accession Number PTA-121711; and (3) *Enterococcus faecium* strain MB505 having ATCC Accession Number PTA-121709. The composition demonstrated the following pathogen inhibition percentages: 90.9% inhibition of *E. coli* O157:H7; 90.0% inhibition of *Salmonella typhimurium* and 94.0% inhibition of *Salmonella enteriditis*.

Another composition is described that includes (1) *Lactobacillus animalis* strain MB101 having ATCC Accession Number PTA-121710; (2) *Lactobacillus animalis* strain MB102 having ATCC Accession Number PTA-121711; (3) *Enterococcus faecium* strain MB505 having ATCC Accession Number PTA-121709; and (4) *Pediococcus acidilactici* strain MB902 having ATCC Accession Number PTA-121712. The composition demonstrated the following pathogen inhibition percentages: 93.1% inhibition of *E. coli* O157:H7; 97.4% inhibition of *Salmonella typhimurium* and 96.0% inhibition of *Salmonella enteriditis*.

Another composition is described that includes (1) *Lactobacillus animalis* strain MB101 having ATCC Accession Number PTA-121710 and (2) *Enterococcus faecium* strain MB505 having ATCC Accession Number PTA-121709. The composition demonstrated the following pathogen inhibition percentages: 92.1% inhibition of *E. coli* O157:H7; 95.8% inhibition of *Salmonella typhimurium* and 95.4% inhibition of *Salmonella enteriditis*.

Another composition is described that includes (1) *Lactobacillus animalis* strain MB101 having ATCC Accession Number PTA-121710; (2) *Enterococcus faecium* strain MB505 having ATCC Accession Number PTA-121709; and (3) *Pediococcus acidilactici* strain MB902 having ATCC Accession Number PTA-121712. The composition demonstrated the following pathogen inhibition percentages: 85.7% inhibition of *E. coli* O157:H7; 87.0% inhibition of *Salmonella typhimurium* and 90.5% inhibition of *Salmonella enteriditis*.

Another composition is described that includes (1) *Lactobacillus animalis* strain MB101 having ATCC Accession Number PTA-121710 and (2) *Pediococcus acidilactici* strain MB902 having ATCC Accession Number PTA-121712. The composition demonstrated the following pathogen inhibition percentages: 92.7% inhibition of *E. coli* O157:H7; 96.3% inhibition of *Salmonella typhimurium* and 95.4% inhibition of *Salmonella enteriditis*.

Another composition is described that includes (1) *Lactobacillus animalis* strain MB101 having ATCC Accession Number PTA-121710; (2) *Lactobacillus animalis* strain MB102 having ATCC Accession Number PTA-121711; and (3) *Pediococcus acidilactici* strain MB902 having ATCC Accession Number PTA-121712. The composition demonstrated the following pathogen inhibition percentages: 90.8% inhibition of *E. coli* O157:H7; 89.7% inhibition of *Salmonella typhimurium* and 94.0% inhibition of *Salmonella enteriditis*.

Another composition is described that includes (1) *Lactobacillus animalis* strain MB102 having ATCC Accession Number PTA-121711 and (2) *Enterococcus faecium* strain MB505 having ATCC Accession Number PTA-121709. The composition demonstrated the following pathogen inhibition percentages: 86.3% inhibition of *E. coli* O157:H7; 87.1% inhibition of *Salmonella typhimurium* and 90.8% inhibition of *Salmonella enteriditis*.

Another composition is described that includes (1) *Lactobacillus animalis* strain MB102 having ATCC Accession Number PTA-121711; (3) *Enterococcus faecium* strain MB505 having ATCC Accession Number PTA-121709; and (4) *Pediococcus acidilactici* strain MB902 having ATCC Accession Number PTA-121712. The composition demonstrated the following pathogen inhibition percentages: 91.6% inhibition of *E. coli* O157:H7; 90.7% inhibition of *Salmonella typhimurium* and 94.8% inhibition of *Salmonella enteriditis*.

Another composition is described that includes (1) *Lactobacillus animalis* strain MB102 having ATCC Accession Number PTA-121711 and (2) *Pediococcus acidilactici* strain MB902 having ATCC Accession Number PTA-121712. The composition demonstrated the following pathogen inhibition percentages: 84.4% inhibition of *E. coli* O157:H7; 82.7% inhibition of *Salmonella typhimurium* and 87.9% inhibition of *Salmonella enteriditis*.

Another composition is described that includes (1) *Enterococcus faecium* strain MB505 having ATCC Accession Number PTA-121709 and (2) *Pediococcus acidilactici* strain MB902 having ATCC Accession Number PTA-121712. The composition demonstrated the following pathogen inhibition percentages: 86.5% inhibition of *E. coli* O157:H7; 87.3% inhibition of *Salmonella typhimurium* and 91.7% inhibition of *Salmonella enteriditis*.

As shown in FIG. 3, *Lactobacillus animalis* strain MB101 having ATCC Accession Number PTA-121710 alone demonstrated the following pathogen inhibition percentages: 93.9% inhibition of *E. coli* O157:H7; 97.9% inhibition of *Salmonella typhimurium*; 97.2% inhibition of *Salmonella enteriditis*; 96.3% inhibition of *E. coli* O121:H19; 94.4% inhibition of *E. coli* O45:H2; 92.8.% inhibition of *E. coli* O103:H11; 93.0% inhibition of *E. coli* O145, 91.9% inhibition of *E. coli* O26:H11; and 85.0% inhibition of *E. coli* O111.

Individually, *Lactobacillus animalis* strain MB102 having ATCC Accession Number PTA-121711 demonstrated the following pathogen inhibition percentages: 90.1% inhibition of *E. coli* O157:H7; 87.8% inhibition of *Salmonella typhimurium*; 93.9% inhibition of *Salmonella enteriditis*; 91.2% inhibition of *E. coli* O121:H19; 90.8% inhibition of *E. coli* O45:H2; 94.7.% inhibition of *E. coli* O103:H11; 87.4% inhibition of *E. coli* O145, 89.3% inhibition of *E. coli* O26:H11; and 85.9% inhibition of *E. coli* O111.

Individually, *Enterococcus faecium* strain MB505 having ATCC Accession Number PTA-121709 demonstrated the following pathogen inhibition percentages: 88.2% inhibition of *E. coli* O157:H7; 87.8% inhibition of *Salmonella typhimurium*; 92.3% inhibition of *Salmonella enteriditis*; 86.6% inhibition of *E. coli* O121:H19; 70.1% inhibition of *E. coli* O45:H2; 88.2.% inhibition of *E. coli* O103:H11; 87.5% inhibition of *E. coli* O145, 86.9% inhibition of *E. coli* O26:H11; and 89.8% inhibition of *E. coli* O111.

Individually, *Pediococcus acidilactici* strain MB902 having ATCC Accession Number PTA-121712 demonstrated the following pathogen inhibition percentages: 85.2% inhibition of *E. coli* O157:H7; 68.3% inhibition of *Salmonella typhimurium*; 87.5% inhibition of *Salmonella enteriditis*; 88.2% inhibition of *E. coli* O121:H19; 88.6% inhibition of *E. coli* O45:H2; 91.5.% inhibition of *E. coli* O103:H11; 86.0% inhibition of *E. coli* O145, 87.3% inhibition of *E. coli* O26:H11; and 86.4% inhibition of *E. coli* O111.

Each of (1) *Lactobacillus animalis* strain MB101 having ATCC Accession Number PTA-121710; (2) *Lactobacillus animalis* strain MB102 having ATCC Accession Number PTA-121711; (3) *Enterococcus faecium* strain MB505 having ATCC Accession Number PTA-121709; and (4) *Pediococcus acidilactici* strain MB902 having ATCC Accession Number PTA-121712 inhibits the growth of *E. coli* O157:H7, *Salmonella typhimurium*; *Salmonella enteriditis*; and the Big-Six *Escherichia coli* strains (referred to as the non-O157 STECs) that include *E. coli* O121:H19; *E. coli* O45:H2; *E. coli* O103:H11; *E. coli* O145, *E. coli* O26:H11; and *E. coli* O111, albeit some more effectively than others.

As an example, and as disclosed above, the constituent bacteria are provided in equal amounts and sum to the same total amount of inhibiting bacteria as pathogenic bacteria that are initially mixed together, before incubation, and inhibition is measured.

Certain aspects of the disclosure contemplate a carrier formulation for the bacterial combinations. The carrier may be any number of different percentages (weight per weight, weight per volume, or volume per volume) of the final product. The carrier can comprise any amount of about 99.9%, about 95%, about 90%, about 80%, about 70%, about 60% about 50%, about 40%, about 30% and so on. The remaining composition can also include other carriers such as lactose, glucose, sucrose, salt, cellulose and the like. In specific aspects of the disclosure, the carrier may be 50% or more of the total product. The carrier can be tailored for the target animal; for instance the carrier can be tailored for feedlot housed cattle, dairy cattle or calves, among others, depending on the particular needs of the target.

The carrier and composition can also have defined properties, such as solubility/insolubility in water or solubility/insolubility in fat and the like.

Other chemicals or materials principally used for the reduction or absorption of moisture may also be included. These may include, but are not limited to: calcium stearate, sodium aluminosilicate, silica, calcium carbonate, zeolite, bicarbonates, sodium sulfate, silicon dioxide, or ascorbic acid.

Other chemicals or materials principally used for the reduction or absorption of oxygen may also be included. These may include, but are not limited to, iron oxides, ascorbic acid, sodium sulfide, and silica materials.

The bacteria mixed with the carrier can be stored in a pouch or bag fabricated from various materials, a bottle fabricated from a variety of materials, a capsule, a box, or other storage container. The composition may also be applied onto a variety of foods including, but not limited to, meats, vegetables, fruits, processed foods, and others for the purpose of pathogen inhibition. The composition can also be packaged as a probiotic supplement for human consumption, particularly when capsulized or made into tablets.

Preservation methods for the bacteria can include a process of freezing, freeze-drying and/or spray-drying. In certain aspects, the preserved bacteria contain a viable cell concentration of $1\times10^8$ to $5\times10^{12}$ cfu/g. Still further, in certain aspects the concentrations range from $5\times10^{10}$ cfu/g to $5\times10^{13}$ cfu/g of bacteria.

In certain instances, a bacterial formulation for administration to a subject or a surface or other target can include a preservation matrix, which contains and preserves the bacterial culture. Such a matrix may include a biologically active binding agent, an antioxidant, a polyol, a carbohydrate and a proteinaceous material. For example, the matrix may have a pH of from about 5.0 to about 7.0. Such a preservation matrix may be capable of maintaining at least about $10^6$ viable cells for a period of at least about 12 months in vitro. In other examples, such a matrix maintains at least about $10^7$ viable cells for a period of at least about 12 months in vitro, and more preferably, at least about $10^8$ viable cells for a period of at least about 12 months in vitro. A preservation matrix may be comprised of ingredients to minimize the damaging effects encountered during the preservation process and to provide functional properties. For example when a *Lactobacillus* strain of the present disclosure is added to a preservation matrix for preservation, it may be converted from an actively growing metabolic state to a metabolically inactive state.

In formulations of the present disclosure wherein a preservation matrix is contemplated, a biologically acceptable binding agent can be used to both affix the bacterial culture or cultures to an inert carrier during a preservation process and to provide protective effects (i.e., maintains cell viability) throughout preservation and storage of the bacterial cells.

Antioxidants included in a preservation matrix may be provided to retard oxidative damage to the bacterial cells during the preservation and storage process.

Polyols (i.e., polyhydric alcohols) included in a preservation matrix may be provided to maintain the native, uncollapsed state of cellular proteins and membranes during the preservation and storage process. In particular, polyols interact with the cell membrane and provide support during the dehydration portion of the preservation process.

Carbohydrates included in a preservation matrix may be provided to maintain the native, uncollapsed state of cellular proteins and membranes during the preservation and storage process. In particular, carbohydrates provide cell wall integrity during the dehydration portion of the preservation process.

A proteinaceous material included in a preservation matrix may provide further protection of the bacterial cell during the dehydration portion of the preservation process. Examples of the proteinaceous materials include, but are not limited to skim milk and albumin.

One example of a method of preserving bacterial cells within a preservation matrix includes coating the cell matrix suspension onto an inert carrier that preferably is a maltodextrin bead. The coated beads can then be dried, preferably by a fluid bed drying method. The coated maltodextrin beads can be stored as a powder, placed into gelatin capsules, or pressed into tablets.

In other formulations of the disclosure, the combinations of strains of bacteria contemplated to be cultured can be formulated as a hard gelatin capsule.

In certain applications, the bacteria cultured with the methods described herein may be placed in a microencapsulation formulation. Such microencapsulation formulations may have applicability for example in administration to subjects via oral, nasal, rectal, vaginal or urethral routes. Spray drying is the most commonly used microencapsulation method in the food industry as it is economical, flexible and produces a good quality product. The process involves the dispersion of the core material into a polymer solution, forming an emulsion or dispersion, followed by homogenization of the liquid, then atomization of the mixture into the drying chamber. This leads to evaporation of the solvent (water) and hence the formation of matrix type microcapsules.

The drying process is carried out in such a manner that a low residual moisture content is present in the dry material. The percentage water content is preferably from about 2 to 3% by weight. This may be achieved by adding a post-drying step subsequent to the spray-drying step. The drying material for this purpose is, for example, post-dried in a fluidized bed.

Instead of the above-described physical post-drying processes, desiccants can also be added to the dry material obtained from the spray-drying.

The content of viable microorganisms is in the range of from about $5 \times 10^5$ to $1 \times 10^{12}$ cfu/g of dry matter. These preparations are also referred to as powder concentrates.

Some end uses require fewer viable microorganisms and are therefore blended to a lower final concentration by mixing the bacteria with larger proportions of inert carrier material.

Some bacteria can survive environmental stresses through the formation of spores. This complex developmental process is often initiated in response to nutrient deprivation. It allows the bacteria to produce a dormant and highly resistant cell. Spores can survive environmental assaults that would normally kill other bacteria. Some stresses that endospores can withstand include exposure to high temperatures, high UV irradiation, desiccation, chemical damage and enzymatic destruction. The extraordinary resistance properties of endospores make them of particular importance because they are not readily killed by many antibacterial treatments. Common bacteria that form spores include species from the *Bacillus* and *Clostridium* genera. Spores formed by these bacteria remain in their dormant state until the spores are exposed to conditions favorable for growth. Spores of the specified bacteria can be beneficially utilized in the disclosed compositions because of their ability to withstand processing methods and can have extended shelf life viabilities. Additionally, bacterial spores can require less processing because they do not require additional steps for preservation such as freeze drying, spray drying, freezing and the like.

The disclosed composition can be fed to ruminal fermentors to reduce scours events, improve animal health and animal productivity. Ruminal fermentors that can benefit from the present disclosure include but are not limited to: cattle, sheep, goats, camels, llama, bison, buffalo, deer, wildebeest, antelope, and any other pre-gastric fermentor. Alternatively, the composition can be fed to cecal fermentors to reduce scours events, improve animal health and animal productivity. Cecal fermentors that can benefit from the present disclosure include but are not limited to: horses, ponies, elephants, rabbits, hamsters, rats, hyraxes, guinea pigs, and any other post-gastric fermentor that using the cecum as the primary location of fermentative digestion. The composition can also be fed to intestinal fermentors to reduce scours events, improve animal health and animal productivity. Intestinal fermentors that can benefit from said disclosure include but are not limited to: humans, pigs, chickens, and other post-gastric fermentor using the large intestine as the primary location of fermentative digestion.

The amount of bacteria administered to the animal feed can be any amount sufficient to achieve the desired increase in animal efficiency and/or animal health. This amount can be anywhere from 1 to $10^{13}$ organisms per kg of animal feed. For example, amounts of about $10^4$ cfu/gram feed, about $5 \times 10^4$ cfu/gram feed, about $10^5$ cfu/gram feed, about $5 \times 10^5$ cfu/gram feed, or ranges between 1 to $10^{13}$ organisms per kg of animal feed can be used. In some embodiments, the dried biological (bacteria) may be administered to an animal through a variety of means including, but not limited to, being distributed in an aqueous solution and subsequently being applied to animal feed, water source, or directly fed to the animal, or through direct application of the product onto animal feed or direct administration or consumption by the animal.

In certain examples of the instant composition, the bacteria and methods of the present disclosure involve two or more bacteria. In certain examples, at least some of the bacteria are lactic acid-producing bacteria. These compositions would be provided in a combined amount effective to achieve the desired effect, for example, the killing or growth inhibition of a pathogenic microorganism. This process may involve administering different strains or species of lactic acid producing microorganisms at the same time. In certain embodiments the different strains or species may be combined into a single formulation for administration. In other embodiments, the different strains or species of lactic acid producing microorganisms may be each in a single formulation for administration. Still in other embodiments, some lactic acid producing microorganism strains or species may be combined into a single formulation and others may be combined into a different formulation.

When more than one inhibiting strain is included in the composition, the several bacterial components may be administered to the animal at the same time or in a sequence sufficiently close together to instill similar effects in the animal as when the bacteria are administered at the same time. When serially administered, it is contemplated that the separate formulations can be administered within about 12-24 hours of each other and, more preferably, within about 6-12 hours of each other. In some situations, it may be desirable to extend the time period for administration significantly such that days or weeks can lapse between the respective administrations.

Various combinations may be employed, for example a formulation containing two species of lactic acid producing microorganisms is "A" and a second formulation containing three species of lactic acid producing microorganisms is "B."

In such embodiments, the administration may be, for example as such: A/B/A, B/A/B, B/B/A, A/B/B, A/B/B, B/A/A, A/B/B/B, B/A/B/B, B/B/B/A, B/B/A/B, A/A/B/B, A/B/A/B, A/B/B/A, B/B/A/A, B/A/B/A, B/A/A/B, A/A/A/B, B/A/A/A, A/B/A/A or A/A/B/A. It is further contemplated that other administrations may be used with three or more different formulations of lactic acid producing microorganisms.

In one example, the composition is designed for continual (once daily, for example) or periodic administration to ruminal fermentors throughout a feeding period in order to reduce the incidence and severity of diarrhea and/or improve overall health and/or inhibit pathogens associated with the animal. In this embodiment, the composition comprises a mixture of probiotic bacteria supplemented with prebiotic substances that can be introduced into the rumen and intestines of a ruminal fermentor.

In another example, the composition is designed for continual or periodic administration to cecal fermentors throughout feeding period in order to reduce the incidence and severity of diarrhea and/or improve overall health and/or inhibit pathogens associated with the animal. In this embodiment, the composition comprises a mixture of probiotic bacteria supplemented with prebiotic substances that can be introduced into the cecum and intestines of a cecal fermentor.

In yet another example, the novel composition is designed for continual or periodic administration to intestinal fermentors throughout the feeding period in order to reduce the incidence and severity of diarrhea and/or improve overall health and/or inhibit pathogens associated with the animal. In this embodiment, the composition comprises a mixture of probiotic bacteria supplemented with prebiotic substances that can be introduced into the intestines of an intestinal fermentor.

A wide range of pathogenic bacteria can be inhibited or eliminated through the disclosed compositions of bacteria such as lactic acid producing probiotic bacteria. Specific examples of infectious diseases or conditions of animals which can be caused by pathogenic bacteria include, but are not limited to: staphylococcal infections (caused, for example, by *Staphylococcus aureus, Staphylococcus epidermis*, or *Staphylococcus saprophyticus*), streptococcal infections (caused, for example, by *Streptococcus pyogenes, Streptococcus pneumoniae*, or *Streptococcus agalactiae*), enterococcal infections (caused, for example, by *Enterococcus faecalis*) diphtheria (caused, for example, by *Corynebacterium diptheriae*), anthrax (caused, for example, by *Bacillus anthracis*), listeriosis (caused, for example, by *Listeria monocytogenes*), gangrene (caused, for example, by *Clostridium perfringens*), tetanus (caused, for example, by *Clostridium tetanus*), botulism (caused, for example, by *Clostridium botulinum*), toxic enterocolitis (caused, for example, by *Clostridium difficile*), bacterial meningitis (caused, for example, by *Neisseria meningitidis*), bacteremia (caused, for example, by *Neisseria gonorrhoeae*), *E. coli* infections (colibacilliocis), including urinary tract infections and intestinal infections, shigellosis (caused, for example, by *Shigella* species), salmonellosis (caused, for example, by *Salmonella* species), *Yersinia* infections (caused, for example, by *Yersinia pestis, Yersinia pseudotuberculosis*, or *Yersinia enterocolitica*), cholera (caused, for example, by *Vibrio cholerae*), campylobacteriosis (caused, for example, by *Campylobacter jejuni* or *Campylobacter fetus*), gastritis (caused, for example, by *Helicobacter pylori*), pseudomonas infections (caused, for example, by *Pseudomonas aeruginosa* or *Pseudomonas mallei*), *Haemophilus influenzae* type B (HIB) meningitis, HIB acute epiglottitis, or HIB cellulitis (caused, for example, by *Haemophilus influenzae*), pertussis (caused, for example, by *Bordetella pertussis*), mycoplasma pneumonia (caused, for example, by *Mycoplasma pneumoniae*), nongonococcal urethritis (caused, for example, by *Ureaplasma urealyticum*), legionellosis (caused, for example, by *Legionella pneumophila*), syphillis (caused, for example, by *Treponema pallidum*), leptospirosis (caused, for example, by *Leptospira interrogans*), Lyme borreliosis (caused, for example, by *Borrelia burgdorferi*), tuberculosis (caused, for example, by *Mycobacterium tuberculosis*), leprosy (caused, for example, by *Mycobacterium leprae*), actinomycosis (caused, for example, by *Actinomyces* species), nocardiosis (caused, for example, by *Nocardia* species), chlamydia (caused, for example, by *Chlamydia psittaci, Chlamydia trachomatis*, or *Chlamydia pneumoniae*), Rickettsial diseases, including spotted fever (caused, for example, by *Rickettsia* ricketsii) and Rickettsial pox (caused, for example, by *Rickettsia akari*), typhus (caused, for example, by *Rickettsia prowazekii*), brucellosis (caused, for example, by *Brucella abortus, Brucella* melitens, or *Brucella suis*), and tularemia (caused, for example, by *Francisella tularensis*).

The invention claimed is:

1. A feedlot animal probiotic feed additive comprising a mixture having an equal number of viable bacteria of each of the following four bacteria: *Lactobacillus animalis* strain MB101 having ATCC Accession Number PTA-121710; *Lactobacillus animalis* strain MB102 having ATCC Accession Number PTA-121711; *Enterococcus faecium* strain MB505 having ATCC Accession Number PTA-121709; and *Pediococcus acidilactici* strain MB902 having ATCC Accession Number PTA-121712; and wherein the mixture has an *E. coli* 0157:H7 growth inhibition rate of at least 93.1% when mixed with an equal number of viable *E. coli* 0157:H7 bacteria relative to the total number of viable bacteria comprised by the four bacteria of the mixture.

2. The feed additive recited in claim 1 wherein the mixture has a *Salmonella typhimurium* growth inhibition rate of at least 97.4% when mixed with an equal number of viable *Salmonella typhimurium* bacteria relative to the total number of viable bacteria comprised by the four bacteria of the mixture.

3. The feed additive recited in claim 2 wherein the mixture has a *Salmonella enteriditis* growth inhibition rate of at least 96.0% when mixed with an equal number of viable *Salmonella enteriditis* bacteria relative to the total number of viable bacteria comprised by the four bacteria of the mixture.

4. The feed additive recited in claim 1 wherein the mixture has a *Salmonella enteriditis* growth inhibition rate of at least 96.0% when mixed with an equal number of viable *Salmonella enteriditis* bacteria relative to the total number of viable bacteria comprised by the four bacteria of the mixture.

5. The feed additive recited in claim 4 wherein the mixture is a growth inhibitor to the non-O157 STEC, Big-Six

*Escherichia coli* strains comprising *E. coli* O121:H19; *E. coli* O45:H2; *E. coli* O103:H11; *E. coli* O145:NM, *E. coli* O26:H11; and *E. coli* O111.

6. The feed additive recited in claim 1 wherein each strain in the mixture is a pathogen growth inhibitor.

7. The feed additive recited in claim 1 wherein each strain in the mixture is an *E. coli* O157:H7 growth inhibitor.

8. The feed additive recited in claim 1 wherein each strain in the mixture is a growth inhibitor to the non-O157 STEC, Big-Six *Escherichia coli* strains including *E. coli* O121:H19; *E. coli* O45:H2; *E. coli* O103:H11; *E. coli* O145:NM, *E. coli* O26:H11; and *E. coli* O111.

9. The feed additive recited in claim 1 wherein each strain in the mixture is a *Salmonella* growth inhibitor.

10. The feed additive recited in claim 1 wherein each strain in the mixture is a *Salmonella typhimurium* growth inhibitor.

11. The feed additive recited in claim 1 wherein each strain in the mixture is a *Salmonella enteriditis* growth inhibitor.

12. A method of administering a probiotic direct fed bacterial feed additive to an animal and inhibiting pathogen growth within the animal's digestive tract, the method comprising: feeding to an animal a mixture having an equal number of viable bacteria of each of the following four bacteria: *Lactobacillus animalis* strain MB101 having ATCC Accession Number PTA-121710; *Lactobacillus animalis* strain MB102 having ATCC Accession Number PTA-121711; *Enterococcus faecium* strain MB505 having ATCC Accession Number PTA-121709; and *Pediococcus acidilactici* strain MB902 having ATCC Accession Number PTA-121712; and wherein the mixture has an *E. coli* O157:H7 growth inhibition rate of at least 93.1% when mixed with an equal number of viable *E. coli* O157:H7 bacteria relative to the total number of viable bacteria comprised by the four bacteria of the mixture.

13. The method recited in claim 12 wherein each strain in the mixture is a pathogen growth inhibitor.

14. The method recited in claim 12 wherein each strain in the mixture is an *E. coli* O157:H7 growth inhibitor.

15. The method recited in claim 12 wherein each strain in the mixture is a growth inhibitor to the non-O157 STEC, Big-Six *Escherichia coli* strains including *E. coli* O121:H19; *E. coli* O45:H2; *E. coli* O103:H11; *E. coli* O145:NM, *E. coli* O26:H11; and *E. coli* O111.

16. The method recited in claim 12 wherein each strain in the mixture is a *Salmonella* growth inhibitor.

17. A probiotic food for feedlot housed animals including animal feed mixed with a composition comprising a mixture having an equal number of viable bacteria of each of the following four bacteria: *Lactobacillus animalis* strain MB101 having ATCC Accession Number PTA-121710; *Lactobacillus animalis* strain MB102 having ATCC Accession Number PTA-121711; *Enterococcus faecium* strain MB505 having ATCC Accession Number PTA-121709; and *Pediococcus acidilactici* strain MB902 having ATCC Accession Number PTA-121712; and wherein the mixture has an *E. coli* O157:H7 growth inhibition rate of at least 93.1% when mixed with an equal number of viable *E. coli* O157:H7 bacteria relative to the total number of viable bacteria comprised by the four bacteria of the mixture.

18. The probiotic food for feedlot housed animals recited in claim 17 wherein the mixture has a *Salmonella typhimurium* growth inhibition rate of at least 97.4% when mixed with an equal number of viable *Salmonella typhimurium* bacteria relative to the total number of viable bacteria comprised by the four bacteria of the mixture.

19. The probiotic food for feedlot housed animals recited in claim 17 wherein each strain in the mixture is a pathogen growth inhibitor.

20. The probiotic food for feedlot housed animals recited in claim 17 wherein each strain in the mixture is an *E. coli* O157:H7 growth inhibitor.

21. The probiotic food for feedlot housed animals recited in claim 17 wherein each strain in the mixture is a growth inhibitor to the non-O157 STEC, Big-Six *Escherichia coli* strains including *E. coli* O121:H19; *E. coli* O45:H2; *E. coli* O103:H11; *E. coli* O145:NM, *E. coli* O26:H11; and *E. coli* O111.

22. The probiotic food for feedlot housed animals recited in claim 17 wherein each strain in the mixture is a *Salmonella* growth inhibitor.

23. The probiotic food for feedlot housed animals recited in claim 17 wherein each strain in the mixture is a *Salmonella typhimurium* growth inhibitor.

24. The feed additive of claim 4, wherein said equal number of viable bacteria is from $5 \times 10^5$ to $1 \times 10^{12}$ cfu/gram of dry matter.

25. The method of claim 12, wherein said equal number of viable bacteria is from $5 \times 10^5$ to $1 \times 10^{12}$ cfu/gram of dry matter.

26. The probiotic food of claim 17, wherein said equal number of viable bacteria is from $5 \times 10^5$ to $1 \times 10^{12}$ cfu/gram of dry matter.

* * * * *